US011020082B2

(12) United States Patent
Ojelund (10) Patent No.: US 11,020,082 B2
(45) Date of Patent: *Jun. 1, 2021

(54) METHOD OF REDUCING THE X-RAY DOSE IN AN X-RAY SYSTEM

(71) Applicant: 3SHAPE A/S, Copenhagen (DK)

(72) Inventor: Henrik Ojelund, Kgs. Lyngby (DK)

(73) Assignee: 3SHAPE A/S, Copenhagen K (DK)

( * ) Notice: Subject to any disclaimer, the term of this patent is extended or adjusted under 35 U.S.C. 154(b) by 0 days.

This patent is subject to a terminal disclaimer.

(21) Appl. No.: 16/701,604

(22) Filed: Dec. 3, 2019

(65) Prior Publication Data
US 2020/0107797 A1 Apr. 9, 2020

Related U.S. Application Data (63) Continuation of application No. 16/452,601, filed on Jun. 26, 2019, now Pat. No. 10,524,759, which is a (Continued)

(30) Foreign Application Priority Data

Mar. 27, 2015 (DK) ............................ PA 2015 70179

(51) Int. Cl.
*A61B 6/00* (2006.01)
*G06K 9/00* (2006.01)
(Continued)

(52) U.S. Cl.
CPC ............ *A61B 6/542* (2013.01); *A61B 5/1127* (2013.01); *A61B 5/721* (2013.01); *A61B 6/032* (2013.01);
(Continued)

(58) Field of Classification Search
USPC ........ 382/100, 103, 106–107, 128–134, 154, 382/162, 168, 173, 181, 193, 199, 220,
(Continued)

(56) References Cited

U.S. PATENT DOCUMENTS 5,023,894 A * 6/1991 Yamashita ............ A61B 5/1114
378/162
9,616,251 B2 4/2017 Filiberti et al.
(Continued)

FOREIGN PATENT DOCUMENTS

WO 2013127005 A1 9/2013
WO 2014033614 A1 3/2014
WO 2014120734 A1 8/2014

OTHER PUBLICATIONS

PCT International Search Report (ISA/210) for PCT/EP2016/056387 dated Jun. 27, 2016; 4 pages.
(Continued)

*Primary Examiner* — Seyed H Azarian
(74) *Attorney, Agent, or Firm* — Buchanan Ingersoll & Rooney P.C.

(57) ABSTRACT

A method of reducing the x-ray dose of a patient in an x-ray system includes defining a region of interest of the patient, obtaining at least two tracking images of a tracking element taken with at least one camera having a known positional relationship relative to an x-ray source and/or sensor, determining any movement of the tracking element between the acquisition of at least two tracking images, adjusting the collimator of the x-ray source to compensate for any movement of the tracking element between the acquisition of the at least two tracking images, providing that the field of exposure of the x-ray source is confined to the region of interest and obtaining at least one x-ray image of the region of interest after the adjustment of the collimator.

13 Claims, 4 Drawing Sheets

Related U.S. Application Data continuation of application No. 15/561,739, filed as application No. PCT/EP2016/056387 on Mar. 23, 2016, now Pat. No. 10,376,231.

(51) Int. Cl.
    *A61B 6/03*     (2006.01)
    *A61B 6/04*     (2006.01)
    *A61B 6/14*     (2006.01)
    *A61B 5/11*     (2006.01)
    *A61B 5/00*     (2006.01)

(52) U.S. Cl.
CPC .......... *A61B 6/0487* (2020.08); *A61B 6/0492* (2013.01); *A61B 6/14* (2013.01); *A61B 6/469* (2013.01); *A61B 6/488* (2013.01); *A61B 6/501* (2013.01); *A61B 6/545* (2013.01); *A61B 6/547* (2013.01); *A61B 6/486* (2013.01); *A61B 6/582* (2013.01)

(58) Field of Classification Search
USPC ....... 382/225, 232, 254, 274, 285–291, 305, 382/320; 600/1; 378/4, 21, 162, 16, 148
See application file for complete search history.

(56) References Cited

U.S. PATENT DOCUMENTS

| 2007/0280422 | A1 | 12/2007 | Setala |
| 2011/0194670 | A1 | 8/2011 | Borghese et al. |
| 2013/0315374 | A1 | 11/2013 | Gertner et al. |
| 2014/0037174 | A1 | 2/2014 | Ernst et al. |
| 2014/0107390 | A1 | 4/2014 | Brown et al. |
| 2015/0018668 | A1 | 1/2015 | Mershon et al. |
| 2015/0243025 | A1* | 8/2015 | Berlinger ............... A61B 6/486 382/131 |
| 2017/0106206 | A1* | 4/2017 | Seckel .................. A61K 8/361 |
| 2017/0106208 | A1 | 4/2017 | Gauthier et al. |
| 2018/0192146 | A1* | 7/2018 | Lian ....................... G10L 15/22 |
| 2020/0004342 | A1* | 1/2020 | Isaacs ................... A61B 6/547 |

OTHER PUBLICATIONS

PCT Written Opinion of the International Searching Authority (ISA/237), for PCT/EP2016/056387, dated Jun. 27, 2016; 6 pages.

PCT Notification of Receipt of Record Copy (IB/301), for PCT/EP2016/056387, dated Apr. 12, 2016; 1 page.

PCT First Notice Informing the Applicant of the Communication of the International Application (To Designated Offices Which Do Not Apply the 30 Month Time Limit Under Article 22(1)), (IB/308), for PCT/EP2016/056387, dated Oct. 27, 2016; 1 page.

PCT Second Notice Informing the Applicant of the Communication of the International Application (To Designated Offices Which Do Not Apply the 30 Month Time Limit Under Article 22(1)), (IB/308), for PCT/EP2016/056387, dated Jul. 27, 2016; 1 page.

PCT Notification Concerning Submission , Obtention or Transmittal of Priority Document (IB/304), for PCT/ EP2016/056387, dated Jun. 13, 2016; 1 page.

* cited by examiner

METHOD OF REDUCING THE X-RAY DOSE IN AN X-RAY SYSTEM

CROSS REFERENCE TO RELATED APPLICATIONS

This application is a continuation of U.S. application Ser. No. 16/452,601, filed on Jun. 26, 2019, which is a continuation of U.S. application Ser. No. 15/561,739, filed on Sep. 26, 2017, now U.S. Pat. No. 10,376,231, which is a national stage application of International Application No. PCT/EP2016/056387, filed on Mar. 23, 2016, and which claims the priority of Danish Patent Application No. PA 2015 70179, filed on Mar. 27, 2015. The contents of U.S. application Ser. No. 16/452,601, U.S. application Ser. No. 15/561,739, International Application No. PCT/EP2016/056387, and Danish Patent Application No. PA 2015 70179 are incorporated herein by reference.

TECHNICAL FIELD

This invention generally relates to a system and method for controlling the collimator in a medical imaging device. More particularly, the invention relates to the tracking of patient movements during image acquisition in a medical imaging device, in particular in Cone Beam Computed Tomography (CBCT) scanners, and using this information to direct the x-rays to a defined Region of Interest (ROI).

BACKGROUND

Computed tomography, particularly x-ray computed tomography (CT), is a widely used volumetric imaging principle. In general terms, a radiation source and a radiation-sensitive image sensor are arranged on a line, with the subject of the examination positioned in between. The subject attenuates the radiation. The source-detector arrangement is typically moved into several positions, often on a circle or segment thereof, around the subject of the examination, and images are taken at every position. The spatial, volumetric distribution of the attenuation coefficient within the subject can then be reconstructed from all images, for example using the filtered back projection algorithm, generating a 3D digital model of the subject. Often, the image sensor is a 2D sensor, such as in cone beam computed tomography (CBCT). In medicine, x-ray CT scanners are valuable non-invasive diagnostic devices.

A major concern related to the use of CT scanners in medicine is radiation dose. Accordingly, a large body of research has focused on volumetric reconstruction algorithms that exploit the image data in an optimal way, allowing fewer images to be taken, or a lower dose per image, for a given quality of the reconstruction. While filtered back projection is a direct algorithm, many refined algorithms are iterative ones. Because the volumetric reconstruction problem is ill-posed, various regularization approaches have been suggested, e.g., total variation. Maximum-likelihood estimation has also been proposed, for example with a prior based on material assumptions. Several proposed reconstruction algorithms contain some of the above elements, or all of them.

Another way to lower the needed dose in a CBCT system is to make sure the patient does not move during image acquisition. This is because for a given needed accuracy, the signal-to-noise ratio will be greater when the patient does not move. Also, when the patient moves, motion artifacts such as for example streaks and aliasing may deteriorate the image quality. Therefore, in general, the image quality will be better when patient movement is kept to a minimum.

In prior art CBCT systems, various forms of head fixation devices have been employed to keep the patient fixated during the x-ray recording. These systems all have the goal of minimizing effects from motion blur and patient movement, thereby achieving a higher accuracy of the final images. However, all these systems have the disadvantage that it may be uncomfortable for the patient to be fixated for the duration of the scan, in particular for patients that may suffer from claustrophobia. It therefore remains a problem to achieve a high accuracy of CBCT images without having to fixate the patient.

Yet another way to lower the used dose in a CBCT system is to accurately define a region of interest (ROI). Many existing CT scanners allow the selection of a region of interest, but the selection is made schematically, and in order to ascertain that the relevant volume is covered, the region of interest suggested by the system is often larger than necessary for a particular patient. Also, since there is a risk that the patient moves during x-ray image acquisition, the chosen ROI is often larger than ideally necessary, in order to make certain that the whole ROI is covered in a single scan. It may be useful if the CT scanner allowed realization of the adjustment of the region of interest by for example four independent collimator shutters for the top, bottom, left, and right sides of the beam.

SUMMARY

In one aspect there is disclosed a method of obtaining medical images of a patient using a medical imaging device, the method comprising:
  defining a region of interest of the patient;
  obtaining at least two tracking images of a tracking element taken with at least one camera having a known positional relationship relative to a radiation source and/or sensor;
  determining any movement of the tracking element between the acquisition of at least two tracking images;
  adjusting the medical imaging device based on the determined movement of the tracking element between the acquisition of the at least two tracking images so that the radiation passes through the region of interest; and
  obtaining at least one medical image of the region of interest after the adjustment of the medical imaging device.

In this way, it is insured that even if the patient moves during the acquisition of medical images, the radiation is confined to the region of interest, thereby making it possible to for example define a smaller region of interest.

In another aspect there is disclosed a method of obtaining one or more x-ray images of a patient, the method comprising:
  defining a region of interest of the patient;
  obtaining at least two tracking images of a tracking element taken with at least one camera having a known positional relationship relative to an x-ray source and/or sensor;
  determining any movement of the tracking element between the acquisition of at least two tracking images;
  adjusting the collimator of the x-ray source to compensate for any movement of the tracking element between the acquisition of the at least two tracking images, providing that the field of exposure of the x-ray source is confined to the region of interest; and obtaining at least one x-ray image of the region of interest after the adjustment of the collimator.

In X-ray optics, a collimator is a device that filters a stream of rays so that only those traveling parallel to a specified direction are allowed through. Collimators are used in X-ray optics because it is not yet possible to focus radiation with such short wavelengths into an image through the use of lenses as is routine with electromagnetic radiation at optical or near-optical wavelengths. Without a collimator, rays from all directions will be recorded; for example, a ray that has passed through the top of the specimen but happens to be travelling in a downwards direction may be recorded at the bottom of the plate, resulting in a blurred image.

Accordingly, it is thus possible to compensate for any unwanted movement the patient makes during acquisition of the x-ray images. The movement of the tracking element corresponds to a movement of the patient, and since there is a feedback between the determination of the movement of the tracking element and the collimator, it is possible to focus the x-rays on the region of interest, even if the patient has moved.

In some embodiments a scout image is taken of the patient. The scout image may be taken with a lower resolution/image quality using the x-ray source and sensor, or the scout image may be taken using a surface imaging device, for example using a face scanner, an intra-oral scanner and/or a surface contour laser scanner, and the region of interest is defined using the scout image.

In this way, the region of interest chosen will correspond to the exact geometry of the patient, rather than using a generic or standard geometry to define the region of interest.

In some embodiments, the predefined information of the tracking element comprises at least one fiducial marker, such as a plurality of fiducial markers in a predefined pattern, size, shape and/or colour.

When the placement, size, shape and/or colour of the fiducial markers are already known with very high accuracy before any images are taken, it is possible to determine with very high accuracy the movement of the tracking element between images. In prior art systems, landmarks on the patient have been used to track any movement of the patient. However, this is not as accurate as using a tracking element, for example comprising fiducial markers placed on the tracking element with a very high and known placement, because unlike in the current disclosure, the landmarks have to first be determined or marked by an operator or by computer software. This means that the exact position of the landmarks will not be as accurate as using a tracking element. Also, when taking for example a series of chest x-rays, the breathing of the person will affect the relative positions of the landmarks, so that this in itself will lead to a less accurate result.

In some embodiments, the tracking images and the x-ray images are time stamped using the same clock.

One way to correlate the movement of the patient with the x-ray data, is to map the movement of the tracking element in time with the recording of the x-ray data. In principle, the cameras recording the tracking element and the x-ray sensor could be run using two separate processors with each their own clock. However, in this case, the two clocks would have to be synchronized in order to be able to map exactly the movement of the patient with the medical imaging data. A simpler solution is to have both the cameras and the x-ray device run using the same clock. This can be accomplished for example by running the cameras and the x-ray device from the same computer processor. The computer processor may be a stand-alone desktop or laptop computer or any other type of computer means, or it may be integrated in the scanner.

In some embodiments, determining the position and orientation of the tracking element at each time stamp comprises:
  recognizing a plurality of the individual fiducial markers in each tracking image;
  obtaining a digital representation in a database of the known predefined pattern and/or shape of the fiducial markers;
  recognizing the pattern of the fiducial markers in each image to achieve a best fit to the known predefined pattern of the fiducial markers on the tracking element from each tracking image.

In order to determine the orientation and position of the tracking element, image analysis algorithms can be used. For example, if the fiducial markers are in the form of dots of a known size, the algorithms can be used to detect where there are dots and what size they have. The method used may for example be principal component analysis (PCA), although other methods are also possible and known to the person skilled in the art.

Since the fiducial markers have a known size, shape and/or predefined pattern on the tracking element, once the size, shape and position of each found dot is determined, a mask comprising the known predefined pattern of the fiducial markers can by loaded from a database, be overlayed on the tracking image, and the fit of the tracking image to the mask can be determined, thereby finding the orientation and position of the tracking element.

In some embodiments there may be more than one camera, such as two cameras or three cameras for recording the movement of the tracking element. The reason for this, is that if only one camera is used, it is difficult to unambiguously determine how far away from the camera the fiducial marker is. If two cameras are used, it is difficult to unambiguously determine the position of the tracking element in a direction that is parallel to a line connecting the two cameras. If, on the other hand, three cameras are used, possibly but not necessarily, placed for example at the points of an equilateral triangle, the position of the tracking element in all three dimensions can be unambiguously determined.

Determining the position and orientation of the tracking element using three cameras, can be accomplished for example by having the images from the three cameras time stamped so that at each time t, there are three images taken of the element, recognizing the fiducial markers in each image, determining a best fit to the known predefined pattern of the fiducial markers on the tracking element in each image, determining the position and orientation of the tracking element in each of the three images of the tracking element at each time stamp, and computing a weighted average of the position and orientation of the tracking element from the three images.

In some embodiments, determining the position and orientation of the tracking element at each time stamp comprises:
  recognizing a plurality of the individual fiducial markers in each tracking image;
  using classification of the indices of the fiducial markers; and
  matching the known pattern of the fiducial markers on the tracking element to the pattern of the fiducial markers on the tracking image using the classification of the indices of the fiducial markers.

Matching the known pattern of the fiducial markers may for example be accomplished using a computer device, where the tracking images are loaded, and the fiducial markers are recognized and/or segmented in the tracking images. Then, the position of the fiducial markers in the tracking image are indexed, and the index of the fiducial markers in the tracking image are compared to the known index of the fiducial markers on the tracking element. Since the distance between the fiducial markers on the tracking element is known, the distances between the fiducial markers in the tracking images can be compared to the known distances, and known mathematical algorithms can be used to determine the position and rotation of the tracking element in the tracking images.

In some embodiments, the camera position and rotation of each camera is calibrated or determined;
the intrinsic parameters such as the focal length, skew, principal point and lens distortion are calibrated or determined for each camera;
the tracking images from the three cameras are acquired simultaneously such that at each time t, there are three images taken of the tracking element;
the fiducial markers are recognized in each tracking image and the position of each fiducial marker is determined directly in the camera co-ordinate frame;
the position and/or orientation of the tracking element from the three images is determined using a cost function to minimize the difference in the determined position of the fiducial markers in each of the tracking images.

Since extrinsic parameters of the cameras are known (i.e. the position and rotation of the cameras with relation to the medical imaging device), and the fiducial markers are recognized in each image and the position of the fiducial markers are determined directly in the co-ordinate frame of the camera, the determination of the position and rotation of the tracking element relative to the medical imaging device will be more accurate.

In some embodiments, the tracking element is attached to a headband, which can be placed on the patient's head. It is an advantage if the headband is adjustable, since it should be possible to securely attach the headband to patients with different head sizes such as children and adults, without any risk of the headband moving during the exposure time.

The tracking element may have only one fiducial marker, but preferably should have a plurality of fiducial markers on its surface, for example in the form of dots or circles. There may be any number of fiducial markers, for example more than 10, more than 100, more than 200 or more than 400 dots. Preferably there should be enough dots to make it simple to find the position and size of the dots, but not so many that it would take too much processing time.

In some embodiments, there are asymmetrical features on the tracking element or the tracking element itself is asymmetrical. In principle, it is possible to determine the position and orientation of the tracking element even if the fiducial markers are all placed in a completely symmetrical pattern. In this case, it would be assumed that the tracking element has moved the shortest possible distance that is consistent with the pattern of the fiducial markers, between each time stamp. However, if the fiducial markers are placed asymmetrically, or if the tracking element itself is asymmetrical, there is no ambiguity in when overlaying the mask of the known predefined pattern with the image of the tracking element.

The adjustment of the collimator should take place substantially in real time during acquisition of the x-ray images. In this way, any movement of the patient will be reflected in the adjustment of the collimator. The adjustment of the collimator may comprise tilting the collimator, moving the collimator in a horizontal and/or vertical direction and/or any other direction, and/or changing any other characteristics of the collimator such as the size of the opening of the collimator.

There are many different designs of collimators, and any collimator can be used with this invention. The collimator may for example be a set of four lead plates that can be individually adjusted, to change the size of the opening and the direction of the x-rays, or it may be a grid of rods that can be adjusted to create a similar effect, or any other design that is capable of directing the x-rays.

The inventive concept of this specification can be used advantageously in any medical imaging device where it is important that the patient is still during imaging, such as standard x-ray, magnetic resonance imaging, positron emission tomography, etc. However, it is particularly useful in CBCT systems where it is very important to get a very high accuracy of the scan, and where it is important to achieve a low dose of x-ray exposure.

In some embodiments, the fiducial markers are in the form of circular dots. Dots or circles are simple geometrical features, that are easily recognized by computer algorithms.

In some embodiments, the x-ray images are combined to form a digital medical model.

In some embodiments, the system may include a mouthpiece for helping the patient stay still during the exposure. The mouthpiece may be in the form of a plate attached to the medical imaging device, and configured to allow the patient to bite onto the plate.

The tracking element in this specification can be made from any material such as plastic, glass, metal or the like. It is, however important that the tracking element is made out of a material that is substantially rigid, so that the known pattern of fiducial markers will not be distorted over time.

In some embodiments, the tracking element is made of coated glass, and the fiducial markers are printed on the surface of the glass. This material is both rigid, and it is relatively simple to etch or print fiducial markers on the surface of the glass with high accuracy.

In some embodiments, disclosed is a method of reducing the x-ray dose of a patient in an x-ray system, the method comprising:
defining a region of interest of the patient;
obtaining a first tracking image of a tracking element taken with at least one camera having a known positional relationship relative to an x-ray source and/or sensor, said tracking images depicting at least a part of the tracking element;
obtaining a second tracking image of the tracking element taken with the at least one camera;
determining any movement of the tracking element between the acquisition of the first and second tracking images;
adjusting the collimator of the x-ray system to compensate for any movement of the tracking element between the acquisition of the first and second tracking images providing that the field of exposure of the x-ray source is confined to the region of interest.

Since the collimator is adjusted to compensate for any movement of the patient, the region of interest can be defined more narrowly than if there was no compensation for the movement of the patient. Therefore, the effective x-ray dose the patient receives will be less than if there was no collimator adjustment.

In some embodiments, the x-ray system is configured to obtain one of a panoramic x-ray image, a cephalometric image, or any other type of 2-dimensional x-ray image.

In some embodiments, the x-ray system is configured to obtain a 3-dimensional digital model of at least a part of the patient, such as for example a CBCT scan.

In this way, the use of the feedback between the tracking element and the collimator of the x-ray source can be used to reduce the dose and/or raise the accuracy of any x-ray image, whether it is a 2D-image or a 3D digital model.

In another aspect, disclosed is a method of controlling the region of interest of a patient imaged using a medical imaging device, the method comprising:

defining a region of interest of the patient;

obtaining a first tracking image of a tracking element taken with at least one camera having a known positional relationship relative to a radiation source and/or sensor, said tracking image depicting at least a part of the tracking element;

obtaining a second tracking image of the tracking element taken with the at least one camera;

determining any movement of the tracking element between the acquisition of the first and second tracking images;

adjusting the position of the radiation source and/or radiation sensor of the medical imaging system to compensate for any movement of the tracking element between the acquisition of the first and second tracking images providing that the field of exposure of the radiation source is confined to the region of interest.

In this way it is possible to confine the field of exposure, for example of an x-ray source to the region of interest on the patient without adjusting the collimator, but instead by changing the geometry of the medical imaging device. For example, in the case of a CBCT system, the x-ray source and x-ray sensor are placed on a ring capable of rotating around the patient. In this way, if the patient has moved as determined from the position of the tracking element in a series of tracking images, the ring containing the x-ray source and sensor can be rotated to better align the x-rays with the region of interest. Of course, depending on the movement of the patient and the exact geometry of the setup of the medical imaging device, the x-ray source may not be confined completely within the region of interest of the patient. However, it will in most cases be better confined to the region of interest using this setup.

In some embodiments, the medical imaging device is a CBCT scanner, and the at least one medical image are x-ray images defining a panoramic trajectory, wherein the method further comprises:

adjusting the CBCT scanner to follow the determined panoramic trajectory based on the determined movement from the tracking element.

In some cases, it is desired to obtain a panoramic x-ray. A panoramic x-ray is a two-dimensional image that captures the entire oral area in one image, including teeth, upper and lower jaws, and the surrounding structures and tissues. When using a CBCT system, a panoramic trajectory is defined, so that the patient is exposed to the x-rays in a predetermined path that allows for capturing the panoramic x-ray. If the patient moves during this time, the panoramic trajectory may no longer be in correspondence with the actual trajectory, meaning that the resulting panoramic image may be blurred. In this case, the panoramic trajectory can be corrected based on the determined movement of the tracking element. This can be accomplished by adjusting the position and/or exposure of the x-ray source and/or sensor based on the determined movement of the tracking element.

In another aspect, disclosed herein is a system for obtaining medical images of a patient, the system comprising:

a medical imaging device comprising;

one or more tracking image cameras configured to take tracking images of a tracking element;

a computer device comprising a microprocessor and a computer readable medium;

a visual display unit;

input means for controlling the medical imaging device;

wherein the computer device is configured to adjust the medical imaging device in response to determined movement of the tracking element.

This system comprises the means for performing the methods according to the previous aspects and embodiments.

In some embodiments, the computer device is configured to adjust the medical imaging device by adjusting a collimator of the medical imaging device.

In this way, the computer device can adjust for example the beam of an x-ray source, by adjusting the collimator of the x-ray machine.

In some embodiments, the computer device is configured to adjust the medical imaging device by changing the geometry of the medical imaging device.

In this case, instead of adjusting a collimator of the medical imaging device, the geometry of the medical imaging device can be changed. For example, in a CBCT scanner, the ring on which the x-ray sensor and x-ray source are attached, the computer device can adjust the position of the ring, so that the x-ray sensor and/or x-ray source are moved relative to the patient.

In the context of this specification, the term medical imaging device covers any device capable of taking medical images of a patient, such as x-ray, magnetic resonance imaging, computed tomography, positron emission tomography, cone beam computed tomography etc.

In the context of this specification, the term tracking element should be understood to mean any device that can be attached to the patient for the purpose of determining their movement, and should therefore not be confined to mean only a flat rectangular piece of metal or plastic. In principle, the form of the tracking element could be for example circular, semi-circular, pyramidal, triangular, or any other shape. The tracking element could even be a complex three dimensional shape, where the shape of the tracking element itself is used as the fiducial markers.

Embodiments

1. A method of obtaining medical images of a patient using a medical imaging device, the method comprising:

defining a region of interest of the patient;

obtaining at least two tracking images of a tracking element taken with at least one camera having a known positional relationship relative to a radiation source and/or sensor;

determining any movement of the tracking element between the acquisition of at least two tracking images;

adjusting the medical imaging device based on the determined movement of the tracking element between the acquisition of the at least two tracking images so that the radiation passes through the region of interest; and obtaining at least one medical image of the region of interest after the adjustment of the medical imaging device.

2. The method according to embodiment 1, wherein adjusting the medical imaging device based on the determined movement of the tracking element between the acquisition of the at least two tracking images comprises adjusting the collimator of the radiation source to compensate for any movement of the tracking element between the acquisition of the at least two tracking images, providing that the field of exposure of the radiation is confined to the region of interest.

3. The method according to embodiment 1, wherein adjusting the medical imaging device based on the determined movement of the tracking element between the acquisition of the at least two tracking images comprises changing the geometry of the medical imaging device, so that either the radiation sensor and/or source is moved relative to the region of interest, based on the determined movement of the tracking element.

4. The method according any of the preceding embodiments, wherein the medical imaging device comprises an x-ray source and sensor, and a scout image is taken with a lower resolution/image quality using the x-ray source and sensor, and the region of interest is defined using the scout image.

5. The method according to any of the preceding embodiments, wherein a scout image is taken using a face scanner, an intra-oral scanner and/or a surface contour laser scanner, and the region of interest is defined using the scout image.

6. The method according to any of the preceding embodiments, wherein the tracking element comprises a predefined geometry and/or predefined information.

7. The method according to any of the preceding embodiments, wherein determining any movement of the tracking element between the acquisition of at least two tracking images comprises;
  recognizing a plurality of fiducial markers in each tracking image;
  obtaining a digital representation in a database of the known predefined pattern and/or shape of the fiducial markers;
  recognizing the pattern of the fiducial markers in each image to achieve a best fit to the known predefined pattern of the fiducial markers on the tracking element from each tracking image.

8. The method according to any of embodiments 1-7, wherein determining any movement of the tracking element between the acquisition of at least two tracking images comprises:
  recognizing a plurality of the individual fiducial markers in each tracking image;
  using classification of the indices of the fiducial markers; and
  matching the known pattern of the fiducial markers on the tracking element to the pattern of the fiducial markers on the tracking image using the classification of the indices of the fiducial markers.

9. The method according to any of the preceding embodiments, wherein the x-ray images are combined to make a digital medical model.

10. The method according to any of the preceding embodiments, wherein the medical imaging device is a cone beam computed tomography scanner.

11. The method according to embodiment 10, wherein the at least one medical image are x-ray images defining a panoramic trajectory, wherein the method further comprises:
  adjusting the CBCT scanner to follow the determined panoramic trajectory based on the determined movement from the tracking element.

12. The method according to embodiment any of the preceding embodiments, wherein the x-ray system is configured to take one of a panoramic x-ray image, a cephalometric image, or any other type of 2-dimensional x-ray image or a CBCT scan of the patient.

13. A system for obtaining medical images of a patient, the system comprising:
  a medical imaging device comprising;
  one or more tracking image cameras configure to take tracking images of a tracking element;
  a computer device comprising a microprocessor and a computer readable medium;
  a visual display unit;
  input means for controlling the medical imaging device;
  wherein the computer device is configured to adjust the medical imaging device in response to determined movement of the tracking element.

14. The system according to embodiment 13, wherein the computer device is configured to adjust the medical imaging device by adjusting a collimator of the medical imaging device.

15. The system according to embodiment 13, wherein the computer device is configured to adjust the medical imaging device by changing the geometry of the medical imaging device.

BRIEF DESCRIPTION OF THE DRAWINGS

The above and/or additional objects, features and advantages of the present invention, will be further described by the following illustrative and non-limiting detailed description of embodiments of the present invention, with reference to the appended drawings, wherein.

DETAILED DESCRIPTION

Figure 1:
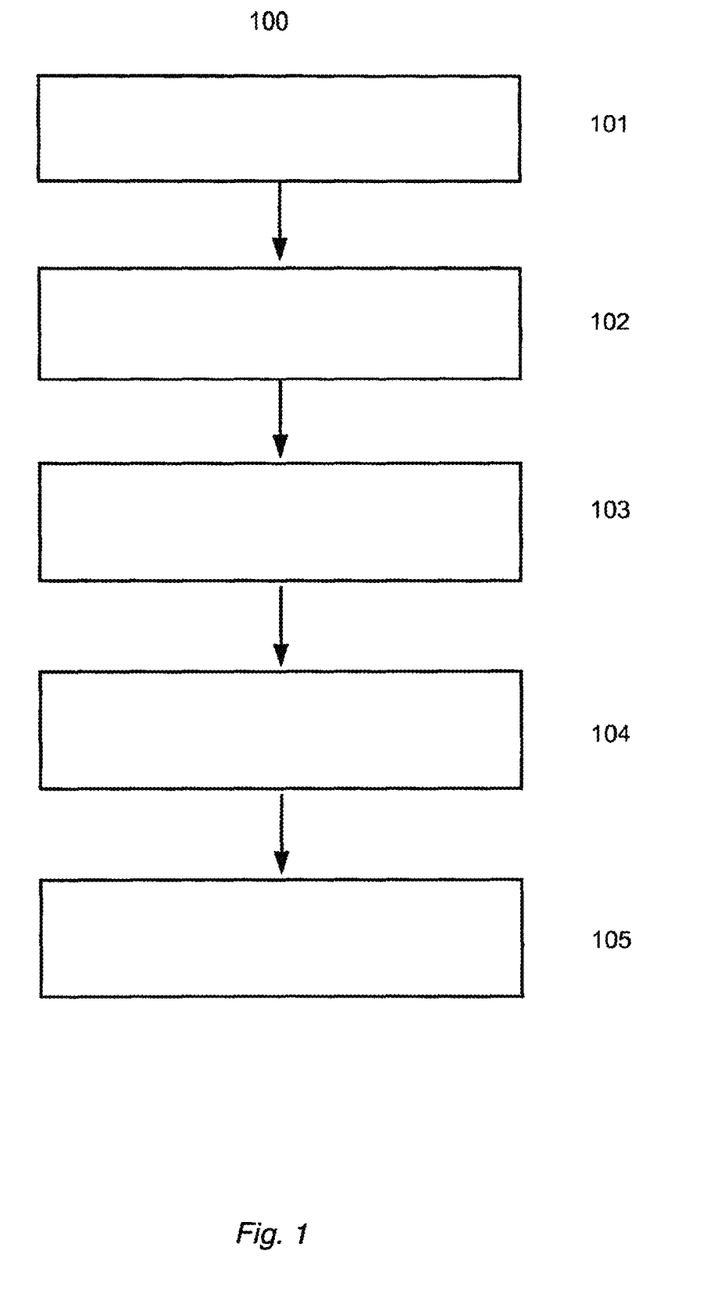
FIG. 1 shows a flow chart of a method according to an embodiment of this invention.

An embodiment of the method disclosed herein is shown in FIG. 1.

In step 101, a scout image is taken of the patient using the x-ray source and sensor, typically at a lower resolution and/or image quality than what is used in the subsequent exposure. Lower resolution and/or image quality may comprise for example using a lower x-ray dose, if the scout image is taken using x-rays. While the scout image is taken, a head tracking system is started. The head tracking system comprises at least one camera, which is configured to take images of a tracking element attached to the head of the patient. The position and orientation of the tracking element is determined in step 102, and at subsequent times, tracking images are taken of the tracking element, and the position and orientation of the tracking element is determined. Based on this determination, the movement of the tracking element, and therefore the movement of the patient, may be determined substantially continuously. In step 103, a region of interest is defined using the scout image. The scout image may for example be displayed on a touch screen or on a computer that has controls for the x-ray scanner, and the region of interest may be defined interactively by the operator, or it may be suggested automatically by the system. Once the region of interest is defined, the resolution of the x-ray scanner may be set to a higher resolution/image quality, if this is needed for the final x-ray images. In step 104, the collimator controlling the path of the x-rays is dynamically adjusted based on the determined movement of the patient, so that the x-rays are confined to expose the region of interest. In this way, even if the patient moves during the x-ray image generation, which could comprise one or more of a CBCT scan, a panoramic image, a cephalometric image or any other type of x-ray, only the region of interest will be subject to x-ray exposure. Therefore, the region of interest can be set to be as small as possible, giving the patient a lower x-ray dose. In step 105, one or more x-ray images at the higher resolution/image quality is taken of the patient using the x-ray scanner. Since the region of interest was defined using the scout image, and the tracking element is attached to the patient during subsequent exposures, any movement of the tracking element can be correlated with a movement of the region of interest.

Figure 2:
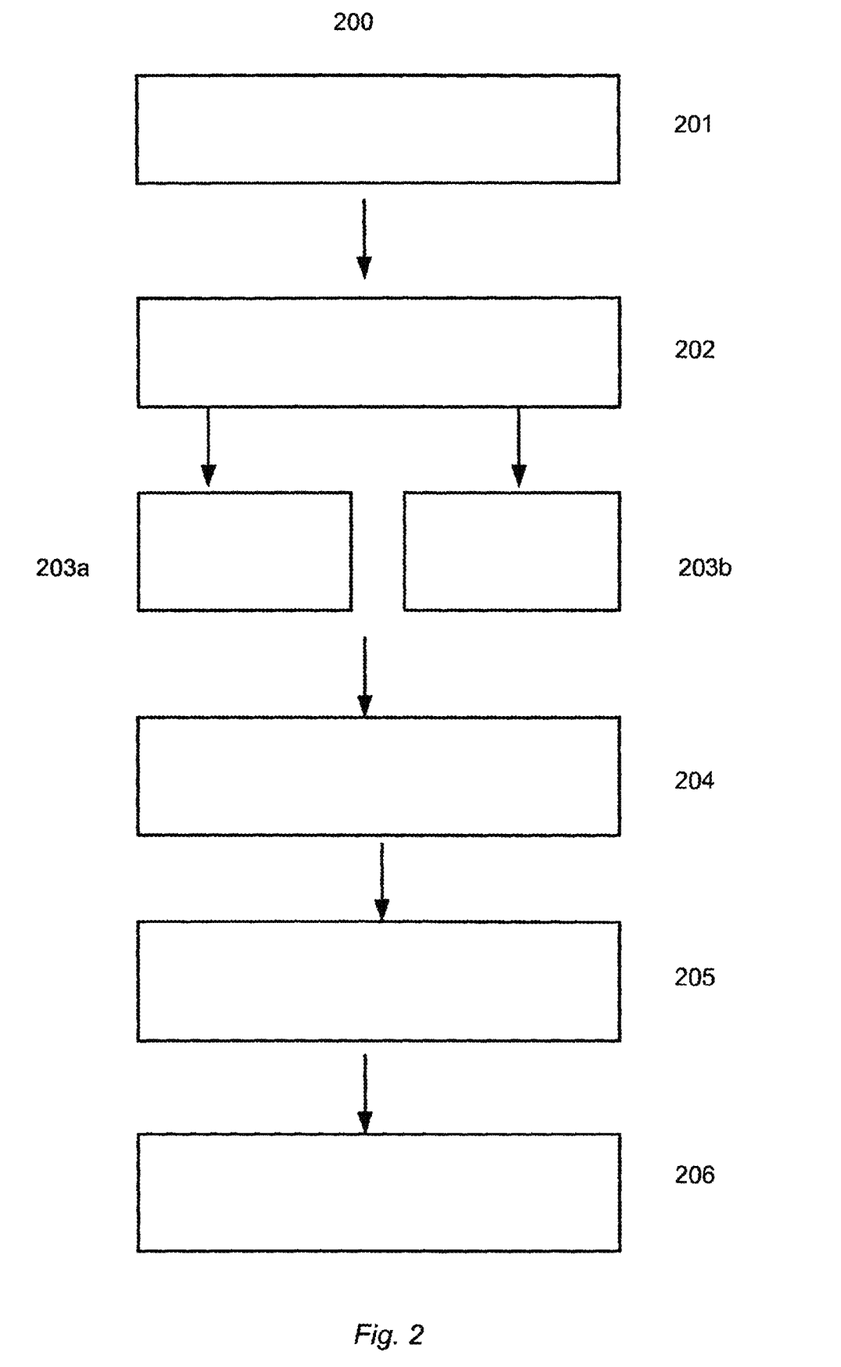
FIG. 2 shows a flow chart of a method according to an embodiment of this invention.
Figure 3:
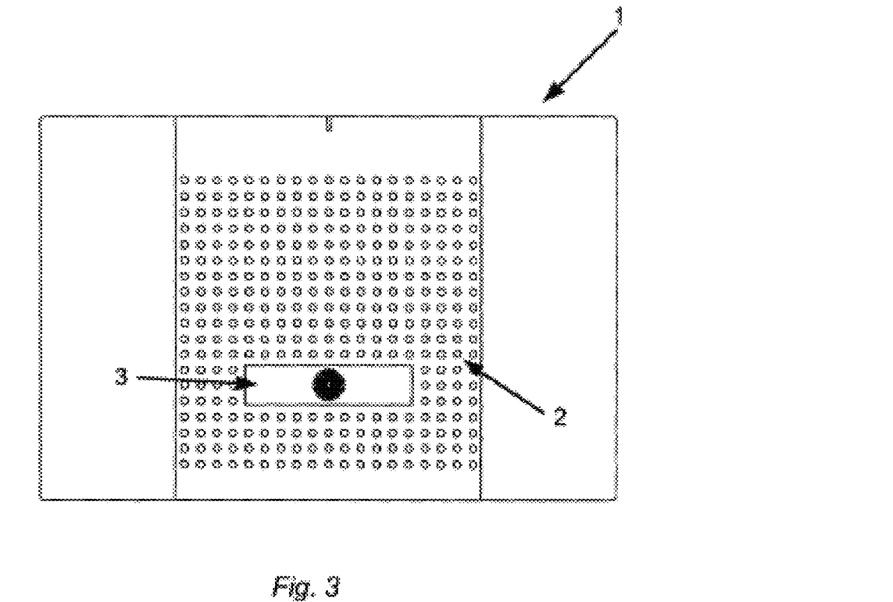
FIG. 3 shows a tracking element according to an embodiment of this invention.

FIG. 2 shows a flow chart representing an embodiment of the method disclosed herein. In step 201, a tracking element, here in the form of a plate, with at least one fiducial marker is attached to the head of a patient. The fiducial markers may be any shape, for example a circle, triangle, ellipse, or any other geometrical shape. In step 202, a scout image is taken using either the x-ray source, a face scanner, a video camera, or any other imaging device. If the scout image is taken using the x-ray source, the scout image will typically be taken with a lower resolution/image quality than the final x-ray images. In step 203a, the medical imaging device acquires medical images of the patient. Concurrently with step 203a, in step 203b, tracking images of the plate are taken using one or more cameras that are placed in a known spatial relationship with the medical imaging source and sensor. The cameras may be integrated into the medical imaging device, or they may be a separate system. In step 204, the position, size and tilt of the fiducial markers is determined. This can for example be done by using principal component analysis. If, for example the fiducial markers are in the form of circular dots, when there is an angle between a normal vector of the plate and a linear axis between the plate and the camera, the circular dots will look slightly deformed in the tracking image. In this case, principal component analysis can be used to determine whether what is observed in the image is a dot, and where the center of the dot is located. In step 205, a mask of the known predefined pattern of the fiducial markers is loaded from a database, and compared with the determined pattern of fiducial markers in each tracking image. This comparison can be done using any method known in the art. This allows the position and orientation of the plate to be determined. It may be advantageous to determine the orientation of the midpoint of the plate, since this will allow the highest accuracy. However, the position and orientation of any point on the plate may be used, for example the corner of the plate.

If there is more than one camera, a tracking image from each camera will be taken at each time t. Each of these tracking images will then have a determined position and orientation of the plate at each time t. The position and orientation determined from each tracking image at time t may be slightly different because of the particular geometry of the situation, for example one camera may have a more acute angle towards the plate than another. The determined position and orientation from each tracking image at time t may then be combined into a single determined position and orientation. This combination can for example be done by performing a weighted average of the position and orientation measurement from each tracking image at time t.

The weighted average can for example be computed by starting with the found position and orientation of the tracking element from one image, determining the difference between this starting position and the position and orientation of the tracking element in each of the other two images, and iteratively adjusting the starting position and orientation of the tracking element to an adjusted position and orientation, until the combined error or difference between the position and orientation of the tracking element in each image and the adjusted position and orientation is minimized.

Alternatively, the starting position and orientation of the tracking element could be a standard default position and orientation, and the difference between this standard position and orientation and the position and orientation determined in each of the three images can be computed. Then the starting position and orientation of the tracking element can be iteratively adjusted until the combined error or difference between the position and orientation of the tracking element in each image and the adjusted starting position is minimized.

Therefore the accuracy of the determined position and orientation of the plate will be better when more than one camera is used.

An alternative approach to the comparison step 205 may be accomplished as follows. Instead of having a database containing a mask of the known predefined pattern of the fiducial pattern or markers, there may instead be a classification of the indices of each of the fiducial markers, as explained in relation to FIG. 3. In this way, the 3D position and orientation of the element is then found such that the classification indices of the known pattern is matched with the determined indices of the fiducial markers on the image sensor after projecting. Here it is important to note that the field of view of each camera, should be large enough to unambiguously determine which part of the element is in the image. In the case of more than one camera, there may be ambiguities as to the exact position and orientation of the element as determined from the tracking images taken with different cameras. In this case, a cost function may be used, so that the position and orientation determination is optimized using information from all cameras.

In step 206, the movement of the plate between different times t is determined, and the determined movement of the plate is correlated to a movement of the region of interest. Since the positional relationship between the cameras and the medical imaging source and sensor is known, any movement of the plate can be directly translated into a corresponding movement of the patient, and therefore the region of interest.

In step 207, any determined movement of the region of interest is used to adjust the collimator so that the x-rays converge on the region of interest. Alternatively, instead of adjusting the collimator, the x-ray source and or sensor may be adjusted or moved based on the determined movement of the region of interest. This will typically be the case if a larger movement of the patient has occurred, for example if the movement is 1*cm* or more. However, no matter the value of the actual determined movement of the patient, the collimator and/or the x-ray sensor and/or the x-ray source may be moved or adjusted.

In FIG. 3, a tracking element 1 according to embodiments of this disclosure is shown. The tracking element has the form of a rectangular plate, made of a rigid material. The plate has a plurality of fiducial markers 2, in a predetermined pattern, layout or configuration. The pattern should be known to a very high degree of accuracy, so that matching subsequent tracking images taken of the plate, can be matched with a mask of the same pattern saved in a database. In CBCT systems today, typical accuracy is in the range 75-350 microns at the moment. Therefore, the accuracy of the known placement of each fiducial marker should at least be within this range in order to achieve a higher accuracy in the digital medical model. Of course, the higher the accuracy of the placement of the fiducial markers, the more the accuracy will be improved.

Each fiducial marker may be classified using a classification index. For example, the fiducial marker closes to one corner could be defined as having the index (0,0), the next one in the same row could have the index (0,1) and in general the fiducial markers could have an index defined as (i,j), with I going from 0 to n, and j going from 0 to m. In this way, the fiducial markers will have a known classification index, which can then be compared to tracking images to match the actual pattern of the fiducial markers on the element to the fiducial markers in the tracking images.

However, when the system is used for example for a cephalometric image or a panoramic image or any 2-dimensional x-ray, a lesser accuracy may be sufficient. For example, if a patient moves several millimeters or centimeters, any accuracy better than the movement of the patient will yield a more accurate final x-ray image/model. The plate may also comprise an asymmetrical feature 3. This will make it easier for computer algorithms to unambiguously match the pattern from the database to the tracking images, and therefrom derive the actual position and orientation of the tracking element in each tracking image. In the case where the fiducial markers are classified using a classification index, the asymmetrical feature will mean that it will be easier to make sure that each tracking camera has a view of the element wherein the position and orientation of the element in the field of view of the camera can more easily be unambiguously derived. That is, once the fiducial markers have been segmented in the tracking images, for example using PCA, they can be classified according to the classification index. If, on the other hand, the field of view of the tracking camera only covered an ambiguous subset of the fiducial markers, it would be impossible to unambiguously derive the position and orientation of the element in the tracking image.

The tracking element may be made of any rigid material such as plastic, metal or glass. When using coated glass for the element, it is easy to print or etch the fiducial markers onto or into the surface of the element.

Although illustrated here as a rigid plate on which the fiducial markers are printed or etched, the tracking element may also for example be a plate with holes, with lights placed underneath the holes, so that the position of the lights can be picked up by a sensor. The lights could for instance use infrared wavelengths, and the sensor could be an infrared sensor. Another option could be to have an active plate where lights are placed on the surface of the plate, and the position of these lights could be picked up by a sensor. For example, the light could be LED lights.

Figure 4:
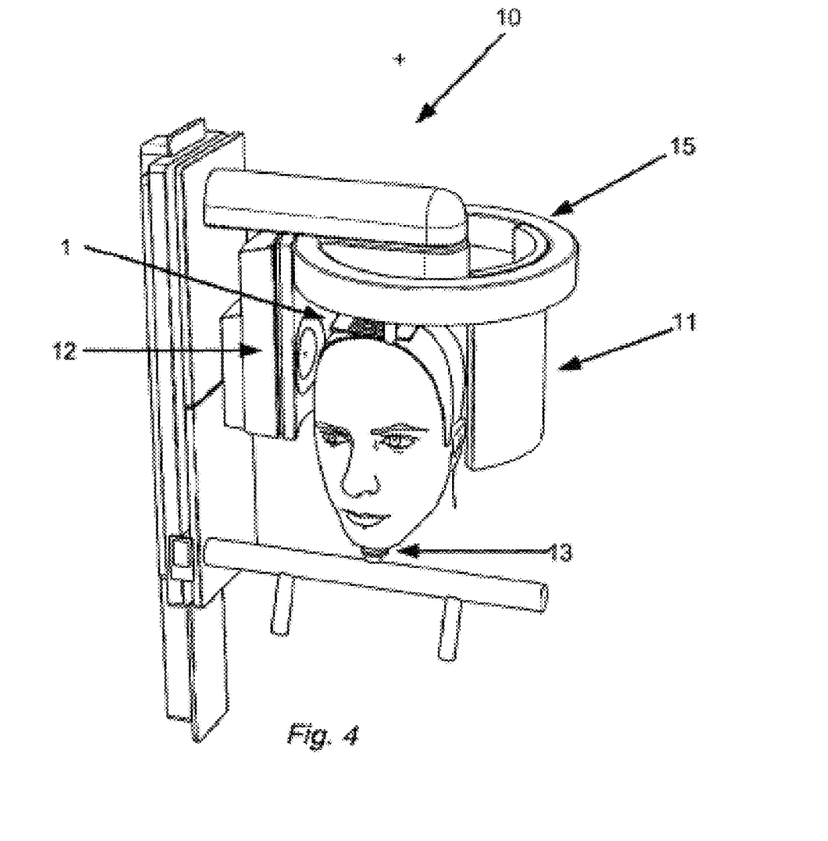
FIG. 4 shows a CBCT scanning system according to an embodiment of this invention.

Turning now to FIG. 4, a system according to an aspect of this disclosure is shown. The system comprises a medical imaging device in the form of a CBCT scanner 10, where the CBCT scanner comprises a sensor 11, and a radiation source 12. The sensor and/or the radiation source are able to turn substantially around a full circle around the patient's head. The system may also comprise a chin rest 13 for the patient to rest his/her chin. The system may also include a face scanner (not shown), the face scanner configured to record a 3D model of the patient's face. The system further comprises a tracking element 1, here shown as a plate attachable to the patient's head. Also comprised in the system is one or more cameras, for example located inside the ring 15. The cameras should be mounted with a known geometrical relationship to the sensor 11 and radiation source 12. Often, this will be near or in the center of the ring 15, since the patient will usually be positioned underneath the center of the ring 15. The cameras are configured to be used to take tracking images of the tracking element 1 simultaneously with the CBCT scanner taking x-ray images. In front of, or integrated in the radiation source is a collimator, which can be adjusted to focus or converge or point the x-rays in a certain direction.

Figure 5:
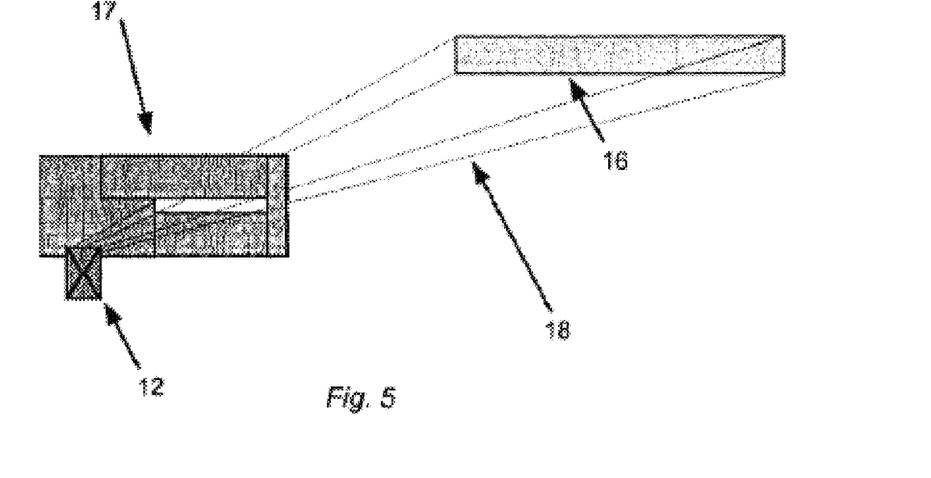
FIG. 5 shows a stylized view of a collimator according to an embodiment of this invention.

FIG. 5 shows a stylized view of the adjustable collimator 17 as disclosed herein. The x-ray source 12 provides x-rays 18, and the collimator 17 is fully adjustable, so that the x-rays 18 can be directed towards the region of interest 16. The collimator can have any form, for example it can be composed of four independent shutters controlling the top, bottom, left and right of the x-ray beam.

Figure 6:
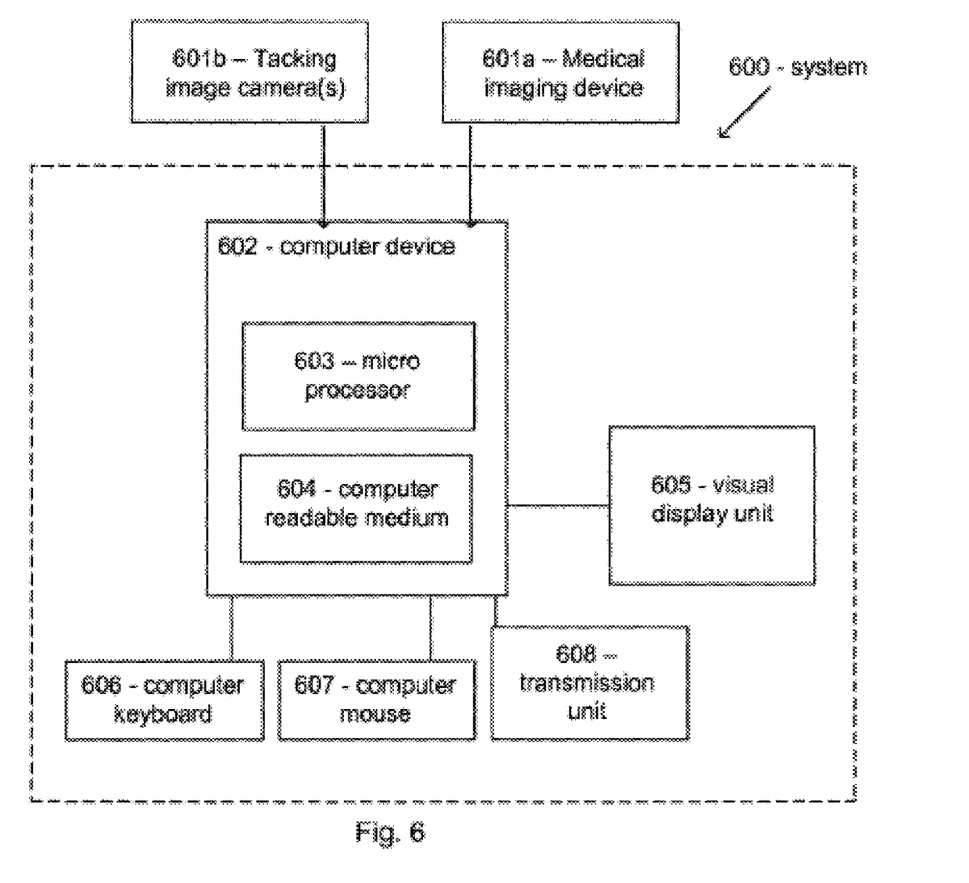
FIG. 6 shows a schematic of a system according to an embodiment of the invention.

FIG. 6 shows a schematic of a system according to an embodiment of the invention. The system 600 comprises a computer device 602 comprising a computer readable medium 604 and a microprocessor 603. The system further comprises a visual display unit 605, input means for entering data and activating digital buttons visualized on the visual display unit 605. In some embodiments as shown here, the input means may be a computer keyboard 606 and a computer mouse 607. The visual display unit 605 can be a computer screen, or a tablet computer, or any other digital display unit. In some cases when the visual display unit is for example a tablet computer, the input means may be the touch screen of the tablet computer.

The computer device 602 is capable of obtaining medical images recorded with one or more medical imaging devices 601a and tracking images recorded by one or more cameras 601b. The obtained medical images and tracking images can be stored in the computer readable medium 604 and provided to the processor 603. In some embodiments system 600 may be configured for allowing an operator to control the medical imaging device using the computer device 602. The controls may displayed digitally on the visual display unit 605, and the user may control the medical imaging device, as well as the tracking cameras using the computer keyboard 606 and computer mouse 607.

The system may comprise a unit 608 for transmitting the medical images, the tracking images and/or the digital medical model via the internet, for example to a cloud storage.

The medical imaging device 601a may be for example a CBCT unit located for example at a dentist office.

Although some embodiments have been described and shown in detail, the invention is not restricted to them, but may also be embodied in other ways within the scope of the subject matter defined in the following claims. In particular, it is to be understood that other embodiments may be utilized and structural and functional modifications may be made without departing from the scope of the present invention.

In device claims enumerating several means, several of these means can be embodied by one and the same item of hardware. The mere fact that certain measures are recited in mutually different dependent claims or described in different embodiments does not indicate that a combination of these measures cannot be used to advantage.

A claim may refer to any of the preceding claims, and "any" is understood to mean "any one or more" of the preceding claims.

The term "obtaining" as used in this specification may refer to physically acquiring for example medical images using a medical imaging device, but it may also refer for example to loading into a computer an image or a digital representation previously acquired.

It should be emphasized that the term "comprises/comprising" when used in this specification is taken to specify the presence of stated features, integers, steps or components but does not preclude the presence or addition of one or more other features, integers, steps, components or groups thereof.

Some features of the method described above and in the following may be implemented in software and carried out on a data processing system or other processing means caused by the execution of computer-executable instructions. The instructions may be program code means loaded in a memory, such as a RAM, from a storage medium or from another computer via a computer network. Alternatively, the described features may be implemented by hard-wired circuitry instead of software or in combination with software.

The invention claimed is:

1. A method of obtaining medical images of a patient using an x-ray source, the method comprising:
   defining a region of interest of the patient;
   obtaining at least two tracking images of a tracking element taken with at least one camera having a known positional relationship relative to at least one of the x-ray source or an x-ray sensor;
   determining any movement of the tracking element between the acquisition of at least two tracking images;
   obtaining a plurality of x-ray images of the region of interest simultaneously with the tracking images; and
   dynamically adjusting a collimator of the x-ray source to compensate for any movement of the tracking element between the acquisition of the at least two tracking images, providing that the field of exposure of the x-ray radiation is confined to the region of interest,
   wherein determining any movement of the tracking element between the acquisition of at least two tracking images comprises:
   recognizing a plurality of fiducial markers in each tracking image;
   obtaining a digital representation in a database of the known predefined pattern or shape of the fiducial markers; and
   recognizing the pattern of the fiducial markers in each image to achieve a best fit to the known predefined pattern of the fiducial markers on the tracking element from each tracking image.

2. The method according to claim 1, wherein a scout image is taken with a lower resolution/image quality using the x-ray source and the x-ray sensor, and the region of interest is defined using the scout image.

3. The method according to claim 1, wherein a scout image is taken using at least one of a face scanner, an intra-oral scanner, and a surface contour laser scanner, and the region of interest is defined using the scout image.

4. The method according to claim 1, wherein the tracking element comprises a predefined geometry or predefined information.

5. The method according to claim 1, wherein determining any movement of the tracking element between the acquisition of at least two tracking images comprises:
   recognizing a plurality of the individual fiducial markers in each tracking image;
   using classification of the indices of the fiducial markers; and
   matching the known pattern of the fiducial markers on the tracking element to the pattern of the fiducial markers on the tracking image using the classification of the indices of the fiducial markers.

6. The method according to any claim 1, wherein the medical images are x-ray images, and wherein the x-ray images are combined to make a digital medical model.

7. The method according to claim 1, wherein the medical images are x-ray images defining a panoramic trajectory.

8. The method according to claim 1, wherein the x-ray source is configured to take one of a panoramic x-ray image, a cephalometric image, or any other type of 2-dimensional x-ray image of the patient.

9. A system for obtaining medical images of a patient, the system comprising:
   an x-ray source;
   one or more tracking image cameras configured to take tracking images of a tracking element;
   a computer device comprising a microprocessor and a non-transitory computer readable medium;
   a visual display unit; and
   input device for controlling the x-ray source;
   wherein the computer device is configured to adjust a collimator of the scanner-ray source in response to determined movement of the tracking element,
   wherein the system is configured to:
   define a region of interest of the patient;
   obtain at least two tracking images of a tracking element taken with at least one camera having a known positional relationship relative to at least one of the ray source or an x-ray sensor;
   determine any movement of the tracking element between the acquisition of at least two tracking images;
   obtain a plurality of x-ray images of the region of interest simultaneously with the tracking images; and
   dynamically adjust a collimator of the x-ray source to compensate for any movement of the tracking element between the acquisition of the at least two tracking images, providing that the field of exposure of the x-ray radiation is confined to the region of interest,
   wherein determining any movement of the tracking element between the acquisition of at least two tracking images comprises:
   recognizing a plurality of fiducial markers in each tracking image;
   obtaining a digital representation in a database of the known predefined pattern or shape of the fiducial markers; and
   recognizing the pattern of the fiducial markers in each image to achieve a best fit to the known predefined pattern of the fiducial markers on the tracking element from each tracking image.

10. The method according to claim 9, wherein the medical images are x-ray images defining a panoramic trajectory.

11. The method according to claim 9, wherein the x-ray source is configured to take one of a panoramic x-ray image, a cephalometric image, or any other type of 2-dimensional x-ray image of the patient.

12. The system according to claim 9, wherein the computer device is further configured to adjust the medical imaging device by changing the geometry of the medical imaging device.

13. A method of reducing the x-ray dose of a patient in an x-ray system, the method comprising:

- defining a region of interest of the patient;
- obtaining a first tracking image of a tracking element taken with at least one camera having a known positional relationship relative to at least one of an x-ray source or an x-ray sensor, said tracking images depicting at least a part of the tracking element;
- obtaining a second tracking image of the tracking element taken with the at least one camera;
- determining any movement of the tracking element between the acquisition of the first and second tracking images;
- adjusting the collimator of the x-ray system to compensate for any movement of the tracking element between the acquisition of the first and second tracking images providing that the field of exposure of the x-ray source is confined to the region of interest, wherein determining any movement of the tracking element between the acquisition of at least two tracking images comprises:

- recognizing a plurality of fiducial markers in each tracking image;
- obtaining a digital representation in a database of the known predefined pattern or shape of the fiducial markers; and
- recognizing the pattern of the fiducial markers in each image to achieve a best fit to the known predefined pattern of the fiducial markers on the tracking element from each tracking image.

* * * * *